United States Patent
Xie et al.

(10) Patent No.: US 11,684,349 B1
(45) Date of Patent: Jun. 27, 2023

(54) FEMALE REPRODUCTIVE SYSTEM SAMPLE COLLECTOR

(71) Applicants: Yanhua Xie, North Haven, CT (US); Yinguang Gao, North Haven, CT (US); Mitchell Brown, North Haven, CT (US)

(72) Inventors: Yanhua Xie, North Haven, CT (US); Yinguang Gao, North Haven, CT (US); Mitchell Brown, North Haven, CT (US)

(*) Notice: Subject to any disclaimer, the term of this patent is extended or adjusted under 35 U.S.C. 154(b) by 0 days.

(21) Appl. No.: 18/167,250

(22) Filed: Feb. 10, 2023

(51) Int. Cl.
*A61B 10/02* (2006.01)
*A61B 10/00* (2006.01)

(52) U.S. Cl.
CPC ...... *A61B 10/0291* (2013.01); *A61B 10/0096* (2013.01); *A61B 2010/0216* (2013.01)

(58) Field of Classification Search
CPC .... A61B 2010/0074; A61B 2010/0216; A61B 10/0291; A61B 10/0096; A61B 10/0233
See application file for complete search history.

(56) References Cited

U.S. PATENT DOCUMENTS

| | | | | |
|---|---|---|---|---|
| 5,795,309 A * | 8/1998 | Leet | ............... | A61B 10/0291 600/569 |
| 8,152,739 B1 * | 4/2012 | McCully | ............ | A61B 10/0291 600/569 |
| 8,968,213 B2 * | 3/2015 | Roush | ............... | A61B 10/0233 600/569 |
| 2005/0277846 A1 * | 12/2005 | Chou | ............... | A61B 10/0291 600/562 |
| 2022/0395259 A1 * | 12/2022 | Thakor | ............. | A61B 10/0096 |

* cited by examiner

*Primary Examiner* — Patrick Fernandes
(74) *Attorney, Agent, or Firm* — RC Trademark Company

(57) ABSTRACT

The present disclosure provides a female reproductive system sample collector, including a sampling device and an elution preservation device, where the elution preservation device is filled with an elution preservation solution, after sampling is completed, the sampling device is submerged in the elution preservation solution of the elution preservation device and sealed for preservation; the sampling device includes a sampling rod and a sheath; the sampling rod includes an operating rod, a straight rod brush and a ball head brush, an opening and closing cover corresponding to the ball head is disposed at a front end of the sheath, and the opening and closing cover includes four oscillating rods that are hinged with a front port of the sheath and the oscillating rods are connected through thin films. The present disclosure can collect cells or nucleic acids of uterus and ovaries in a uterine cavity, a sampling rod can deform in a shape along an outline of the uterine cavity. The sampling rod can avoid sample falling when finishing sampling and recovering; an elution preservation device can prevent liquid from overflowing and leaking or polluting a sealing cap. The present disclosure provides a quick, convenient, widely applicable and less discomfort sample collection channel and a sample protection method for early detection of the ovarian cancer, the endometrial cancer and the cervical cancer.

10 Claims, 14 Drawing Sheets

FEMALE REPRODUCTIVE SYSTEM SAMPLE COLLECTOR

TECHNICAL FIELD

The present disclosure relates to a female reproductive system sample collector.

BACKGROUND

Ovarian and endometrial cancers rank fifth and sixth in female cancer deaths respectively, but because the ovaries are deep in the abdominal cavity, ovarian cancer is mostly asymptomatic in the early stage. Most patients are not diagnosed until later stages, missing the opportunity for early treatment.

According to the statistics, if the ovarian cancer is detected in stage I, the 5-year survival rate is 92%. Unfortunately, only 15% of ovarian cancers are detected in stage I. The survival rate for stage IV patients is only 17%. Thus, the early detection of the ovarian cancer plays a crucial role. Gynecological examination is the best period for early detection of the cancer. However, at present the diagnosis of gynecological examination is still limited to ultrasound B and cervical cell smears, which can realize the detection for the early cervical cancer, but the detection for the endometrial cancer, ovarian cancer and fallopian tube cancers is very limited.

With the development of genome sequencing technology, liquid biopsies using cell-free DNA/RNA have shined a light on the diagnosis of cancer patients and personal precision medicine. This gives doctors the opportunity to find the right targeted drugs, thus achieving the best survival rate and living quality. It particularly brings hopes for many terminal cancer patients. However, early detection remains the real key for the patients and the whole society to achieve a possible cancer "cure".

In order to apply these cutting-edge techniques to the uterus and ovaries located deep in the abdominal cavity, and the method for obtaining uterine and ovarian cell DNA/RNA is the critical part in this work. Researchers have tried peripheral blood and Pap smear methods, but these methods only detect 40% of advanced ovarian cancers, and have no advantages for early detection.

At present, ultrasound B used in gynecological examinations is the ultrasonic wave, but ultrasound images are created by reading the sound waves. These are useful for measurement, but not providing accurate visual effects, so as not to confirm the property of the tissue, and therefore it cannot be used for confirmation.

A cervical liquid-based cell smear can provide the diagnosis of the cervix, but cannot obtain ovary cells deep in the endometrium and abdominal cavity.

Generally, when the cotton sampling is recovered, the sample is easy to fall, with a little amount of collection. The sealing convenience and effectiveness during storage, sample overflow and the like are the technical problems that need to be urgently solved.

SUMMARY

The technical problem to be solved by the present disclosure is to provide a female reproductive system sample collector, which can collect cells or nucleic acids of uterus and ovaries in a uterine cavity. A sampling rod can deform in a shape along an outline of the uterine cavity, with a wide touching range. The sampling rod can avoid sample falling when finishing sampling and recovering; an elution preservation device can prevent liquid from overflowing and leaking or polluting a sealing cap. The present disclosure provides a quick, convenient, widely applicable and less discomfort sample collection channel and a sample protection method for early detection of the ovarian cancer and the endometrial cancer.

In order to implement the above purpose, the technical solution adopted by the present disclosure is a female reproductive system sample collector, including a sampling device and an elution preservation device; an exterior of the sampling device is wholly packaged by a sealing bag, and the elution preservation device is filled with an elution preservation solution. After sampling is completed, the sampling device is submerged in the elution preservation solution of the elution preservation device and sealed for preservation; the sampling device includes a sampling rod and a cylindrical sheath sleeved outside the sampling rod. The sampling rod includes an operating rod, a straight rod brush and a ball head brush which are connected in turn from back to front; the straight rod brush includes a brush rod and bristles planted on the brush rod, and the ball head brush includes a ball body connected to a front end of the brush rod and bristles planed on the ball body; a length of the sheath is greater than or equal to a total length of the straight rod brush and the ball head brush; an outer diameter of the sheath is less than an inner diameter of the elution preservation device; and a via hole is formed in a lower end cover of the sheath, and the operating rod is threaded in the via hole. A front end of the sheath is provided with an opening and closing cover that prevents the loss of the sample, the opening and closing cover corresponds to a position of the ball head brush and includes four oscillating rods that are hinged with a front port of the sheath and in an uniform and circumferential array around a central axis of the sheath, the adjacent two oscillating rods are connected through a thin film, the oscillating rods include upper arc-shaped rods and lower L-shaped rods, and hinge points of the oscillating rods are located at corners of the L-shaped rods. When the opening and closing cover is closed inwards, an orthographic projection length of each arc-shaped rod is greater than that of each L-shaped rod.

Preferably, the bristles of the straight rod brush and the bristles of the ball head brush all include base bristles at the bottom layers and dispersing bristles connected to tail ends of the base bristles, and each base bristle is connected with at least two dispersing bristles; independently and optionally, tail ends of the dispersing bristles are connected with secondary dispersing bristles, and each dispersing bristle is connected with at least two secondary dispersing bristles.

Preferably, the sheath is provided with an inwardly recessed snap ring, the operating rod is provided with a front neck and a rear neck that are inwardly recessed; the front neck and the rear neck are both circular grooves, and the snap ring is matched with the front neck and the rear neck in size; when the straight rod brush and the ball head brush are both in a state of being contained in the sheath, the snap ring is positioned in the front neck; when the straight rod brush is pushed forwards out of the sheath, the snap ring slides from the front neck to the rear neck and is finally clamped in the rear neck; the sheath and the operating rod are locked with each other through the occlusion of the snap ring and the front neck or the rear neck, and foremost and rearmost positions of the operating rod are limited; when the snap ring is arranged between the front neck and the rear neck, the snap ring is in an interference fit contact state with the operating rod; when sampling is finished, the sampling device is retracted into the sheath, then a front end of the sampling device is inserted downwards into the elution preservation device; the sheath and the operating rod are then broken off synchronously from the positions of the snap ring and the front neck, a rear part of the broken position of the sampling device is discarded, and the front part of the broken position of the sampling device is preserved in the elution preservation device for sealing and preservation.

Preferably, a front side wall and a rear side wall of the snap ring are in an inclined shape, and an included angle between the front side wall and the side wall and the side wall of the sheath is 30-70 degrees; a rear side wall of the front neck is in an inclined shape, an included angle between the rear side wall and the side wall of the operating rod is 30-70 degrees, and a front side wall of the front neck is perpendicular to a side wall of the operating rod; a front side wall of the rear neck is in an inclined shape, an included angle between the front side wall and the side wall of the operating rod is 30-70 degrees, and the rear side wall of the rear neck is perpendicular to the side wall of the operating rod.

Preferably, the elution preservation device is a test tube with a sealing cap, which is in threaded connection or buckling connection with the test tube; the operating rod is provided with scale marks, and a zero scale position of each scale mark is a foremost end of the ball head brush; an outside convex sealing ring is disposed on the outer wall of the sheath, a diameter of the sealing ring surpasses an internal diameter of the elution preservation device by at least 1 mm, and the sealing ring is located at the front of the snap ring; the sealing ring not only plays the positioning action at an outer port of cervix when sampling, but also seals the elution preservative solution in the elution preservative device and the effective sampling part on the sampling device below the sealing ring after the sampling is finished.

Preferably, a diameter of the straight rod brush gradually increases from bottom to top; a diameter of the ball head brush is larger than space enclosed by lower ends of the L-shaped rods, so that the ball head brush is prevented from escaping from the clearance of the L-shaped rods when being retracted.

Preferably, the brush rod is an elastic rod, a maximum deflection of a tail end of the brush rod is 4-5 cm, a ball body of the ball head brush is connected with the tail end of the rod brush through a short rod and a ball head hinge, an oscillating angle of the ball head hinge with the axis of the operating rod as a center is less than or equal to 60 degrees, and bristles are also arranged on the short rod; and a bending rigidity EI of the brush rod is calculated according to the following formula:

$$EI = \frac{5ql^4}{384 Y_{max}},$$

where EI is the bending rigidity of the brush rod, q is the uniform distribution force of the inner wall of the uterine cavity to the brush rod, l is the length of the brush rod, and Ymax is the maximum deflection of the brush rod; and an outer wall of a cross section of the sheath is wavy.

Preferably, when an oscillating rod is in a closed state, upper ends of the arc-shaped rods are not mutually abutted; an maximum outward oscillating angle of the oscillating rod in an open status is 40-50 degrees; and when the oscillating rod is completely opened, the thin film is in a tensioned state and an opening and closing cover is in an inverted umbrella shape.

Preferably, a length of the sampling rod is 26±2 cm, a length of the straight rod brush is 3.5±0.5 cm, a diameter of a lower end of the straight rod brush is 0.5 cm, a diameter of an upper end of the straight rod brush is 1 cm, a length of the sheath is 8.0±2.0 cm, and a diameter of the ball head brush is 1±0.5 cm.

Preferably, the ball head hinge includes a ball head and a ball shell sleeved on the ball head, the ball head hinge is provided with a rebounding device, the rebounding device is a spring, one end of the spring is fixed to an edge of the ball shell, the spring is sleeved on the short rod or the brush rod, and the other end of the spring is fixed to the short rod or the brush rod.

Preferably, a handle is arranged at a rear end of the operating rod.

After adopting the above technical solution, the produced beneficial effects are: (1) the uterine and ovarian testing sample collector can collect cells or nucleic acids of the uterus and the ovary in the uterine cavity, the ball head brush at the front end of the sampling rod can, relatively to a free deflection direction of the straight rod brush, prepare for the shape deformation of the straight rod brush along the outline of the uterine cavity, with a wide sampling touch range; (2) under the action of the opening and closing cover, the sampling rod can not only be smoothly pushed out from the sheath, but also prevent the samples on the brush bristle from falling off during recovery; (3) after sampling, the straight rod brush and the ball head brush are contained in the sheath together, the straight rod brush, the ball head brush and the sheath are wholly inserted into the elution preservation device, and the elution preservation device is sealed by the sealing ring on the outer wall of the sheath, so that the elution preservation solution and the samples eluted and preserved in the elution preservation solution are prevented from overflowing and leaking or polluting the sealing cap; (4) the front and rear necks on the operating rod can limit the foremost position and the rearmost position of the sampling rod relative to the sheath, so that the endometrium is prevented from being damaged due to the fact that the sampling rod excessively leans forward during sampling, and the sampling rod is prevented from sliding off the sheath due to the fact that the sampling rod excessively leans backwards during the recovery of the sampling rod; this limiting mode can give an operator an obvious signal during use, and when the snap ring is between the front neck and the rear neck, the snap ring is in an interference fit state with the operating rod, making the process that pushes forward or draws backwards the sampling rod have suitable frictional force, thereby enhancing the operation hand feeling and the sampling stability.

In conclusion, from the above four beneficial effects, the present disclosure provides a quick, convenient, widely applicable and less discomfort sample collection channel and a sample protection method for early detection of the ovarian cancer and the endometrial cancer.

BRIEF DESCRIPTION OF THE DRAWINGS

The present disclosure is further described in detail below in conjunction with the accompanying drawings and specific embodiments.

Figure 1:
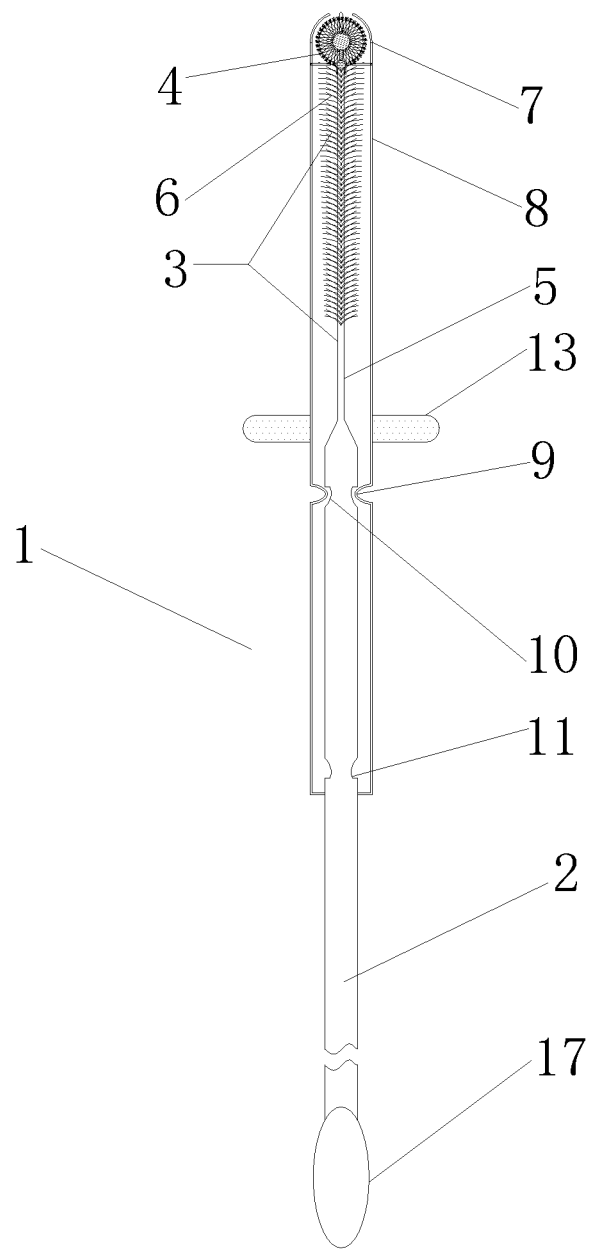
FIG. 1 is a status schematic diagram that a straight rod brush and a ball head brush of a sampling rod are contained in a sheath of the present disclosure.

In the drawing: 1. Sampling device, 2. Operating rod, 3. Straight rod brush, 4. Ball head brush, 5. Brush rod. 6. Bristle, 7. Opening and closing cover, 8. Sheath, 9. Snap ring, 10. Front neck, 11. Rear neck, 12. Elution preservation device, 13. Sealing ring, 14. Short bar, 15. Ball head hinge, 16. Rebounding device, 17. Handle, 18. Break position, 19. Elution preservation solution, 20. Cervix, 21. Uterine cavity, 22. Fallopian tube, 41. Ball body, 61. Base bristle, 62. Dispersing bristle, 63. Secondary dispersing bristle, 71. Oscillating rod, 121. Test tube, 122. Sealing cap, 151. Ball head, 152. Ball shell, 711. Thin film, 712, Arc-shaped rod, 713. L-shaped rod, 714. Hinge point.

DETAILED DESCRIPTION OF THE EMBODIMENTS

Figure 2:
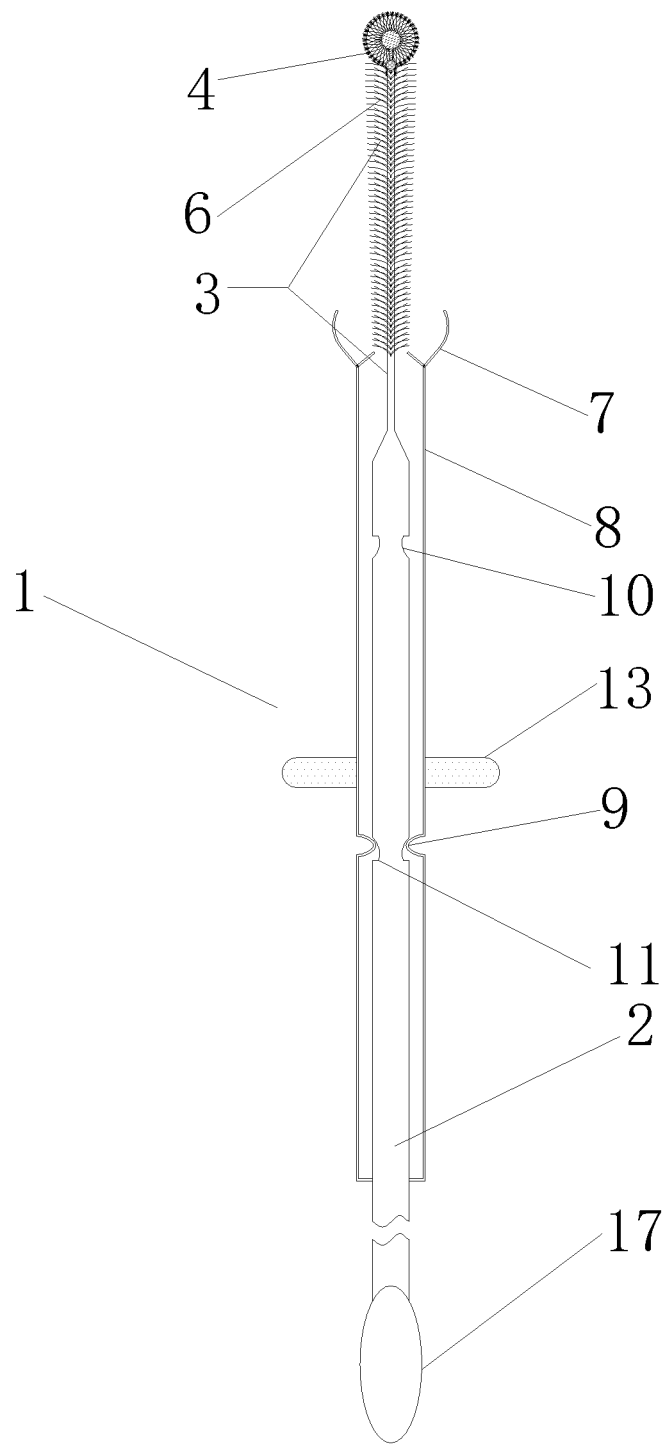
FIG. 2 is a status schematic diagram that a straight rod brush and a ball head brush of a sampling rod are pushed out of a sheath of the present disclosure.
Figure 14:
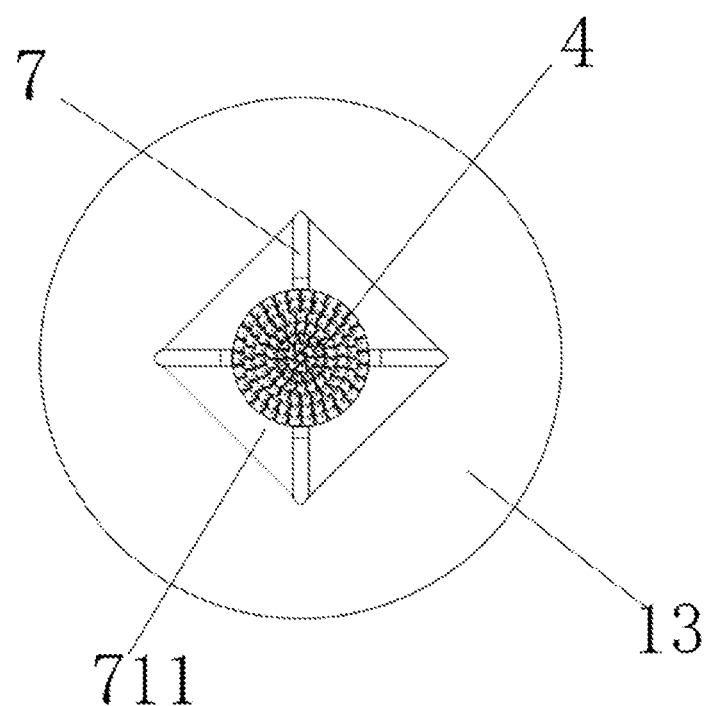
FIG. 14 is a status top view that a straight rod brush and a ball head brush of a sampling rod are pushed out of a sheath of the present disclosure.

Referring to FIG. 1 to FIG. 14, a female reproductive system sample collector provided by the present disclosure includes a sampling device and an elution preservation device; an exterior of the sampling device is wholly packaged by a sealing bag, and the elution preservation device is filled with an elution preservation solution. After sampling is completed, the sampling device is submerged in the elution preservation solution of the elution preservation device and sealed for preservation;

Referring to FIG. 1, FIG. 2 and FIG. 14, the sampling device includes a sampling rod and a cylindrical sheath sleeved outside the sampling rod. The sampling rod includes an operating rod, a straight rod brush and a ball head brush which are connected in turn from back to front; the straight rod brush includes a brush rod and bristles planted on the brush rod, and the ball head brush includes a ball body connected to a front end of the brush rod and bristles planed on the ball body; and before and after sampling, the straight rod brush and the ball head brush are all contained in the sheath, and during sampling, the straight rod brush and the ball head brush are forward pushed out of the sheath.

Referring to FIG. 1, FIG. 2, FIG. 4, FIG. 5 and FIG. 14, a length of the sheath is greater than or equal to a total length of the straight rod brush and the ball head brush; an outer diameter of the sheath is less than an inner diameter of the elution preservation device; and a via hole is formed in a lower end cover of the sheath, and the operating rod is threaded in the via hole. A front end of the sheath is provided an opening and closing cover that prevents the loss of the sample, the opening and closing cover corresponds to a position of the ball head brush and includes four oscillating rods that are hinged with a front port of the sheath and in an uniform and circumferential array around a central axis of the sheath, the adjacent two oscillating rods are connected through a thin film, the oscillating rods include upper arc-shaped rods and lower L-shaped rods, and hinge points of the oscillating rods are located at corners of the L-shaped rods. When the opening and closing cover is closed inwards, an orthographic projection length of each arc-shaped rod is greater than that of each L-shaped rod. The opening and closing cover at the front end of the sheath 8 can open and close, which can not only affect pushing out the sampling rod smoothly, but also prevent the sample on the bristle from falling outside of the sheath when recovery; specifically, when the sheath is returned when the sampling rod finishes sampling, the opening and closing cover forms a funnel-shaped structure with a thick front and a thin rear, the bristles of the sampling rod can only touch the interior of the opening and closing cover, even the sample on the bristles falls, it stays inside the opening and closing cover, so as to ensure the enough sampling amount. When the arc-shaped rods of the opening and closing cover are mutually closed, the front end of the sheath presents a smooth structure to avoid the damage when entering the human body, and the operation is also smoother.

Figure 9:
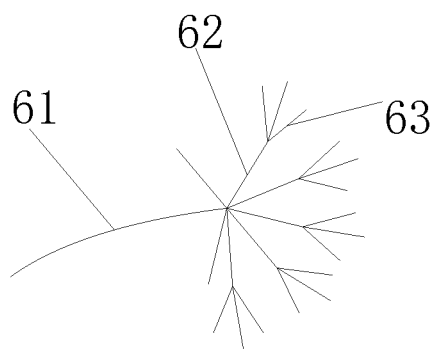
FIG. 9 is an enlarged diagram of a microstructure of bristles of the present disclosure.
Figure 10:
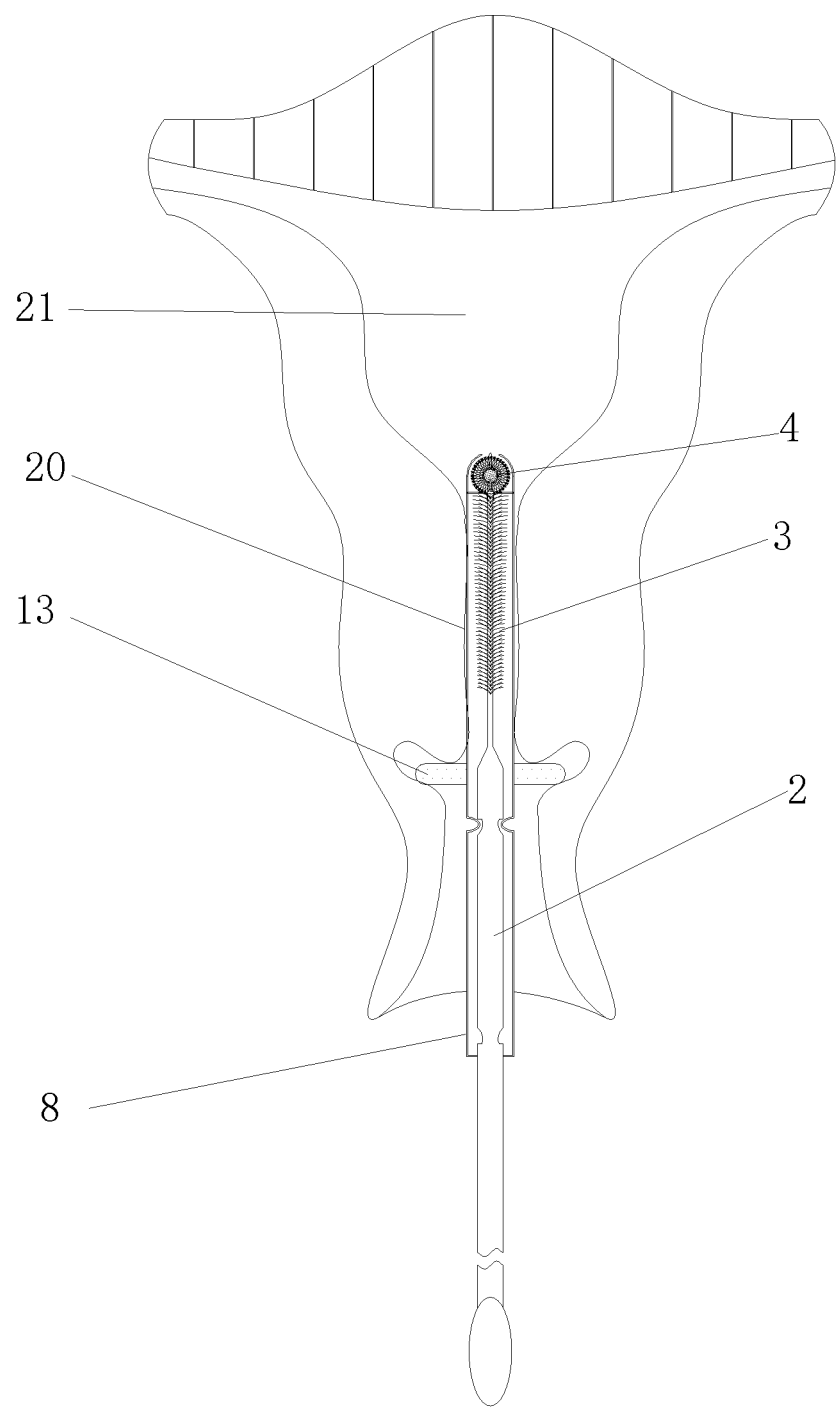
FIG. 10 is a structure schematic diagram that a sheath reaches a sheath reaches a cervical position and a sampling rod is not pushed forward of the present disclosure.
Figure 11:
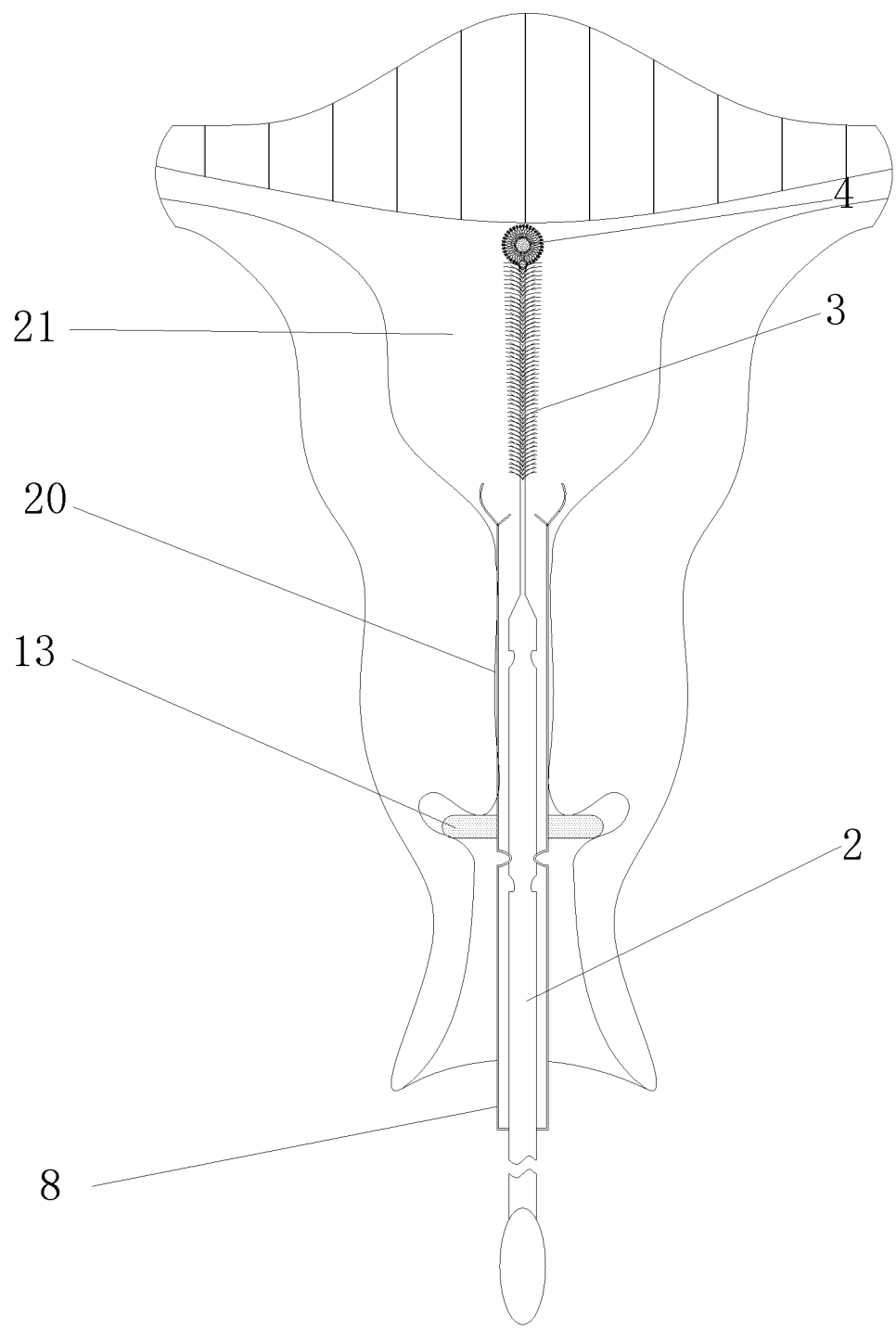
FIG. 11 is a schematic diagram that a sheath is maintained in a cervical position, and a sampling rod samples in a uterine cavity of the present disclosure.
Figure 12:
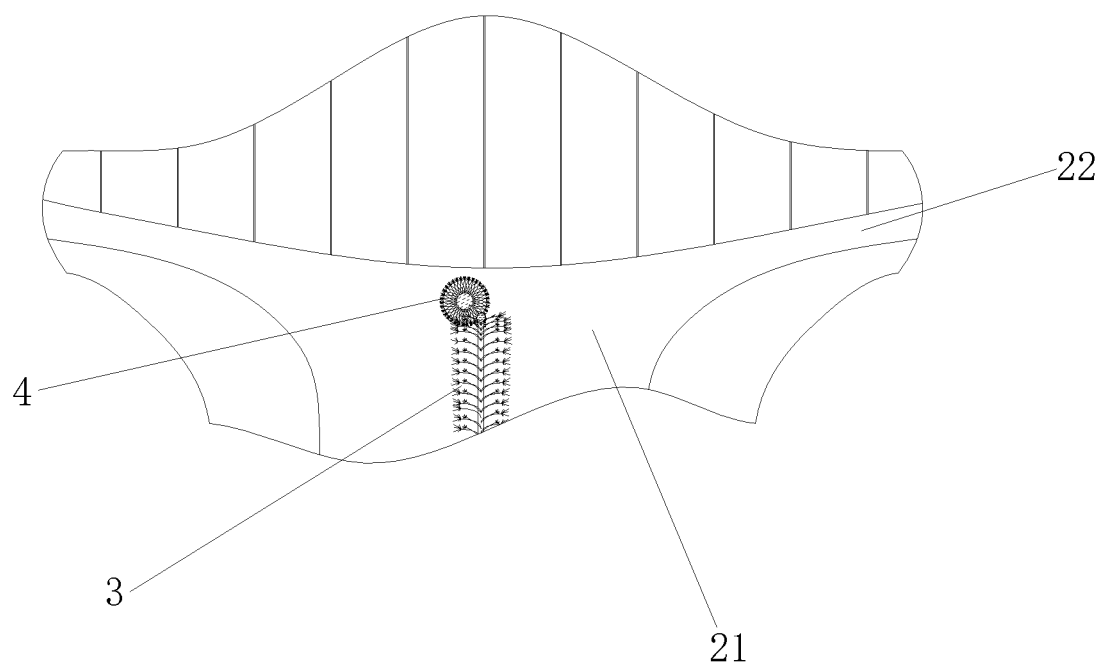
FIG. 12 is a schematic diagram that a sheath is maintained in a cervical position, a ball head brush deflects due to extrusion from a bottom of a uterine cavity, so as to prepare a gesture for bending a straight rod brush of the present disclosure.
Figure 13:
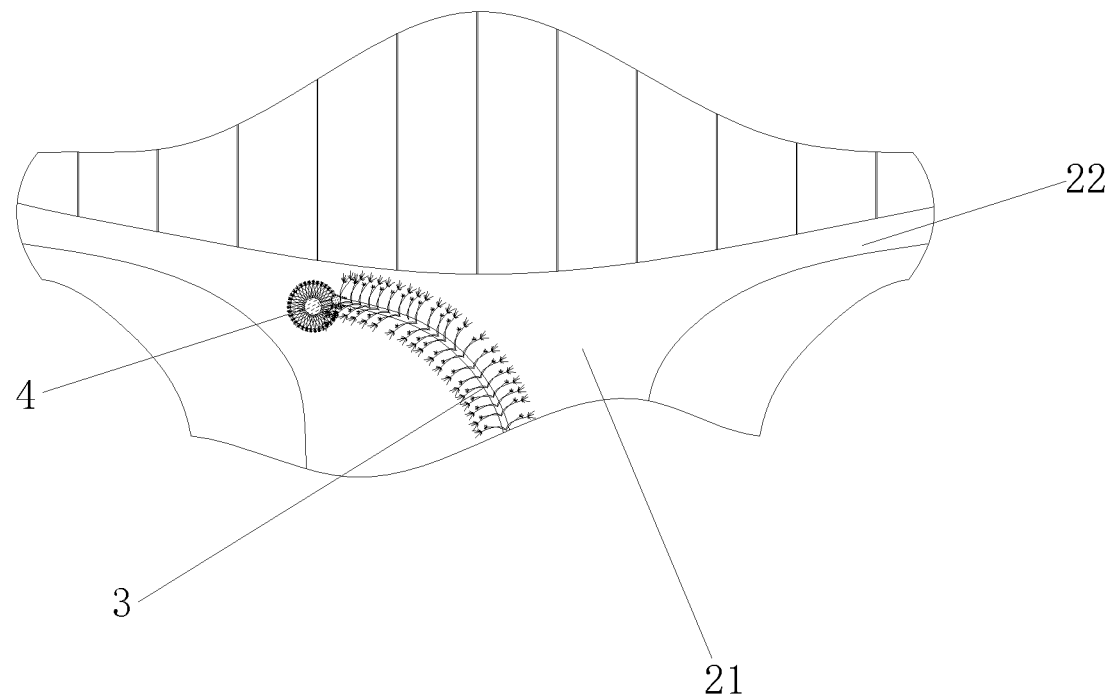
FIG. 13 is a schematic diagram that a sheath is maintained in a cervical position, a straight rod brush bends at a side to collect around a fallopian tube of the present disclosure.

Referring to FIG. 9 separately, the bristles of the straight rod brush and the bristles of the ball head brush all include base bristles at bottom layers and dispersing bristles connected to tail ends of the base bristles, and each base bristle is connected with at least two dispersing bristles; independently and optionally, tail ends of the dispersing bristles are connected with secondary dispersing bristles, and each dispersing bristle is connected with at least two secondary dispersing bristles. The bristles are soft and compact, thereby reducing discomfort, and improving the sampling efficiency.

Figure 3:
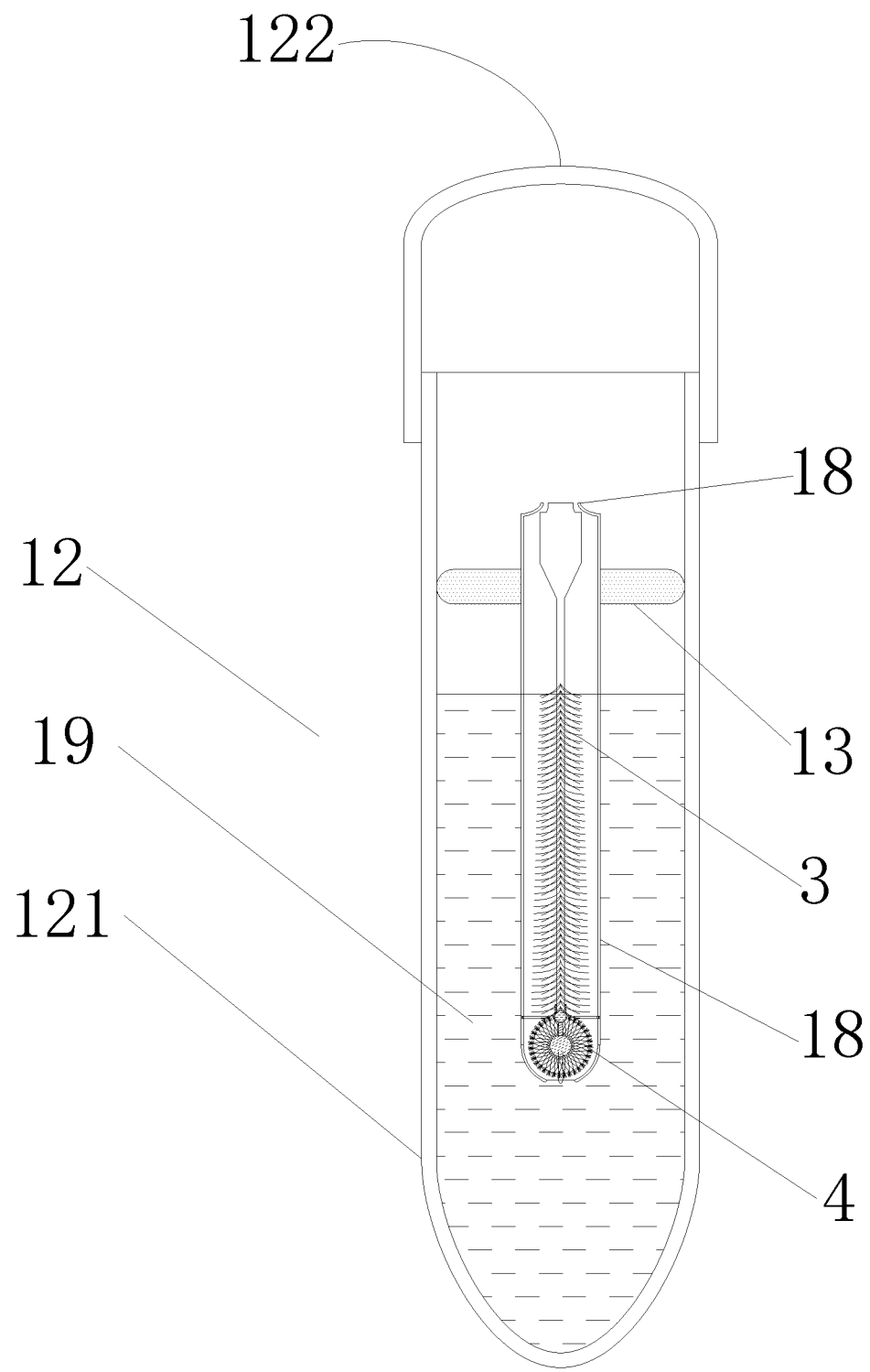
FIG. 3 is a schematic diagram that a broken sampling device is placed in an elution preservation device after sampling of the present disclosure.
Figure 4:
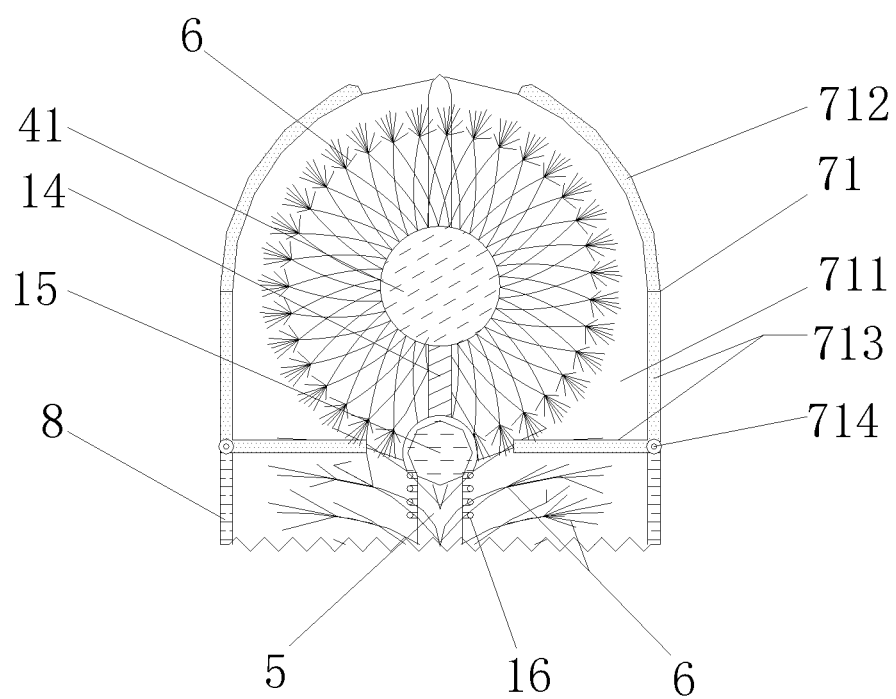
FIG. 4 is a local enlarged diagram that a straight rod brush and a ball head brush of a sampling rod are contained in a front end of a sheath of the present disclosure.
Figure 5:
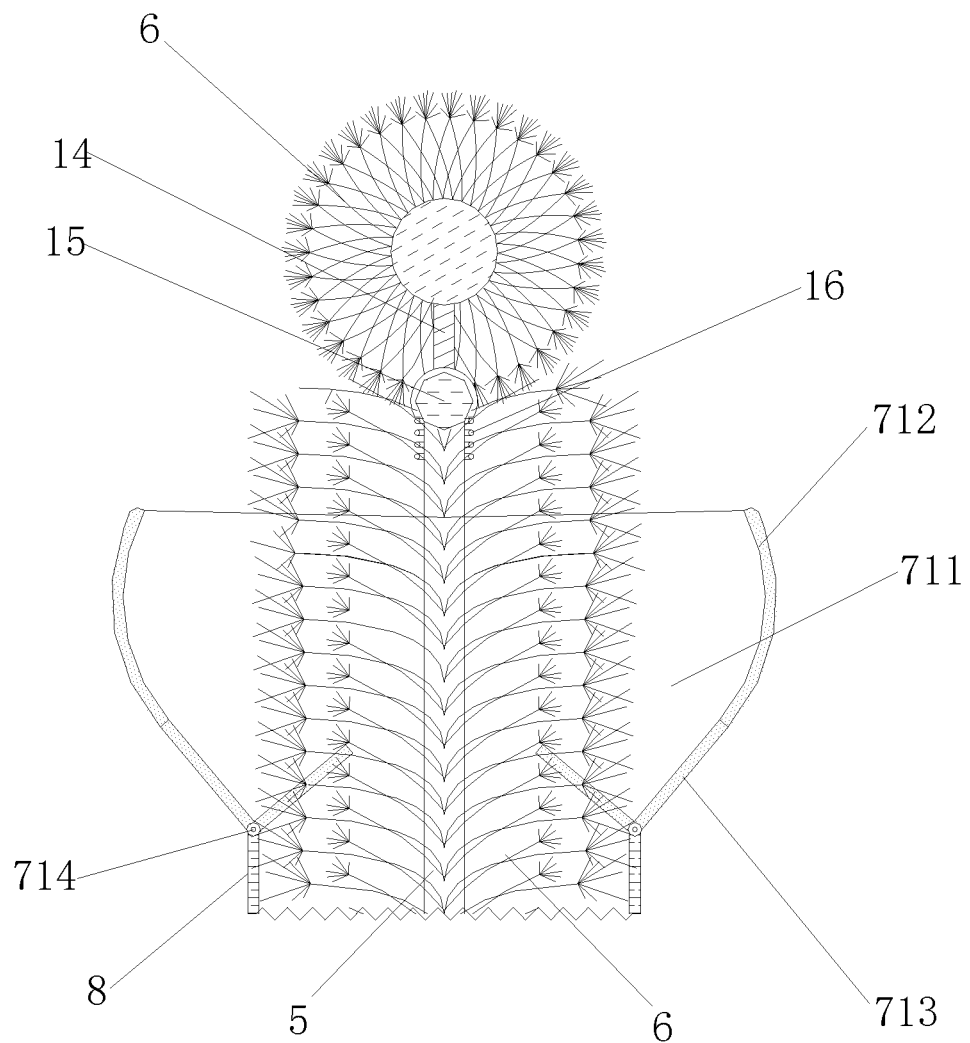
FIG. 5 is a local enlarged diagram that a straight rod brush and a ball head brush of a sampling rod are pushed out of a front end of a sheath of the present disclosure.
Figure 6:
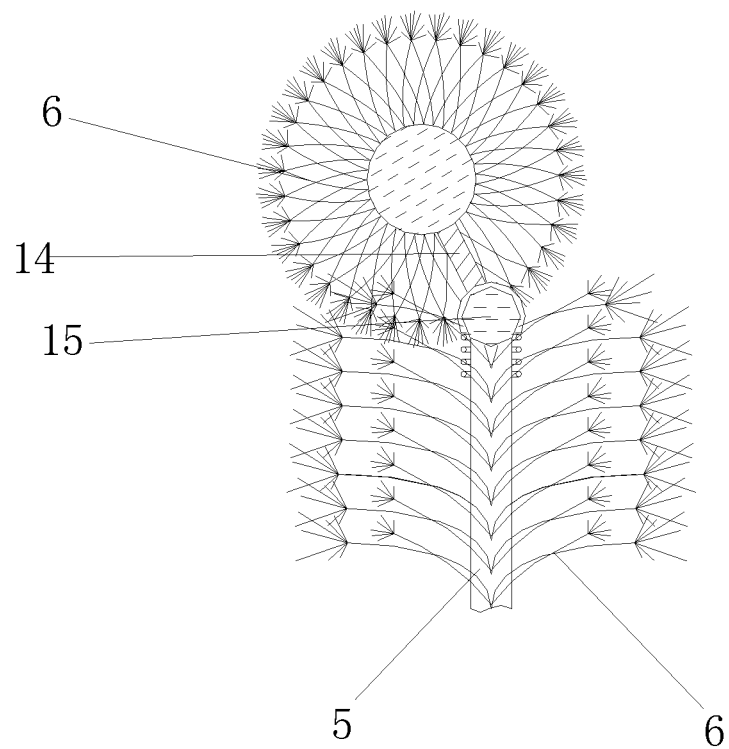
FIG. 6 is a status schematic diagram that a ball head brush deflects due to extrusion from a bottom of a uterine cavity of the present disclosure.

Referring to FIG. 1 to FIG. 3 at the same time, the sheath is provided with an inwardly recessed snap ring, the operating rod is provided with a front neck and a rear neck that are inwardly recessed; the front neck and the rear neck are both circular grooves, and the snap ring is matched with the front neck and the rear neck in size; when the straight rod brush and the ball head brush are both in a state of being contained in the sheath, the snap ring is positioned in the front neck; when the straight rod brush is pushed forwards out of the sheath, the snap ring slides from the front neck to the rear neck and is finally clamped in the rear neck; the sheath and the operating rod are locked with each other through the occlusion of the snap ring and the front neck or the rear neck, and foremost and rearmost positions of the operating rod are limited; when the snap ring is arranged between the front neck and the rear neck, the snap ring is in an interference fit contact state with the operating rod; when sampling is finished, the sampling device is retracted into the sheath, then a front end of the sampling device is inserted downwards into the elution preservation device; the sheath and the operating rod are then broken off synchronously from the positions of the snap ring and the front neck, a rear part of the broken position of the sampling device is discarded, and the front part of the broken position of the sampling device is preserved in the elution preservation device for sealing and preservation.

A front side wall and a rear side wall of the snap ring are in an inclined shape, and an included angle between the front side wall and the side wall and the side wall of the sheath is 30-70 degrees; a rear side wall of the front neck is in an inclined shape, an included angle between the rear side wall and the side wall of the operating rod is 30-70 degrees, and a front side wall of the front neck is perpendicular to a side wall of the operating rod; a front side wall of the rear neck is in an inclined shape, an included angle between the front side wall and the side wall of the operating rod is 30-70 degrees, and the rear side wall of the rear neck is perpendicular to the side wall of the operating rod.

The elution preservation device is a test tube with a sealing cap, which is in threaded connection or buckling connection with the test tube; the operating rod is provided with scale marks, and a zero scale position of each scale mark is a foremost end of the ball head brush; an outside convex sealing ring is disposed on the outer wall of the sheath, a diameter of the sealing ring surpasses an internal diameter of the elution preservation device by at least 1 mm, and the sealing ring is located at the front of the snap ring; the sealing ring not only plays the positioning action at an outer port of cervix when sampling and avoids the sheath being submerged into the uterine cavity, but also seals the elution preservative solution in the elution preservative device and the effective sampling part on the sampling device below the sealing ring after the sampling is finished.

A diameter of the straight rod brush gradually increases from bottom to top; the straight rod brush with the structure characteristics meets the physiological structure of the uterine cavity, and effective sampling is more concentrated on the front section of the straight rod brush and the ball head brush; a diameter of the ball head brush is larger than space enclosed by lower ends of the L-shaped rods, so that the ball head brush is prevented from escaping from the clearance of the L-shaped rods when being retracted. When the ball head is retracted, the L-shaped rods are touched, so that the opening and closing cover is closed.

Preferably, the brush rod is an elastic rod, a maximum deflection of a tail end of the brush rod is 4-5 cm, a ball body of the ball head brush is connected with the tail end of the rod brush through a short rod and a ball head hinge, an oscillating angle of the ball head hinge with the axis of the operating rod as a center is less than or equal to 60 degrees, and bristles are also arranged on the short rod; and a bending rigidity EI of the brush rod is calculated according to the following formula:

$$EI = \frac{5ql^4}{384 Y_{max}},$$

where EI is the bending rigidity of the brush rod, q is the uniform distribution force of the inner wall of the uterine cavity to the brush rod, l is the length of the brush rod, and Ymax is the maximum deflection of the brush rod; and according to the above formula, the material conforming to the requirement of bending rigidity may be quickly selected so as to manufacture the brush rod.

An outer wall of a cross section of the sheath is wavy. The undulating outer wall of the sheath prevents the sheath from adhering to the inner wall of the cervix due to negative pressure.

When the oscillating rods are closed, upper ends of the arc-shaped rods are not touching each other, the maximum angle of the oscillating rod oscillating outwards is 40-50 degrees when the oscillating rods are opened completely, the thin films are in a tensioning state, and the opening and closing cover is in an inverted umbrella shape, ensuring that the bristles only touch the inner surface of the opening and closing cover when the sampling rod is retracted.

A profile formed when the oscillating rods are closed is a hemispherical shape with a hole in a top center, the ball head brush is spherical or ellipsoidal.

A length of the sampling rod is 26±2 cm, a length of the straight rod brush is 3.5±0.5 cm, a diameter of a lower end of the straight rod brush is 0.5 cm, a diameter of an upper end of the straight rod brush is 1 cm, a length of the sheath is 8.0±2.0 cm, and a diameter of the ball head brush is 1±0.5 cm.

Preferably, a handle is arranged at a rear end of the operating rod.

Figure 7:
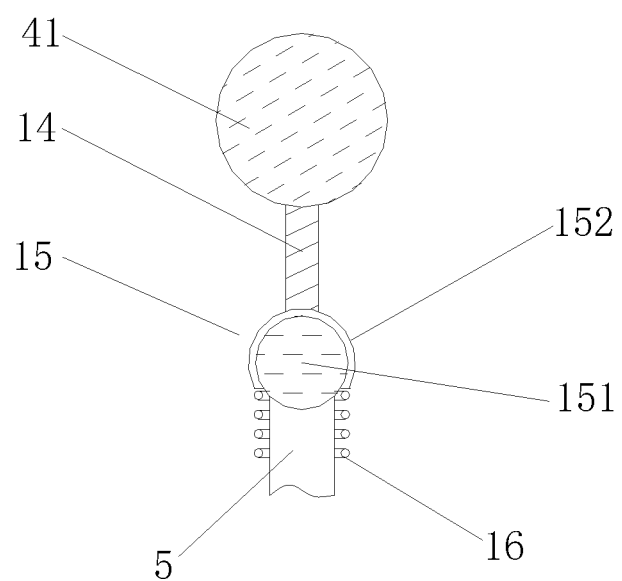
FIG. 7 is an installation schematic diagram of a rebounding device after removing bristles in Embodiment I of the present disclosure.

Referring to FIG. 7 separately, the ball head hinge includes a ball head and a ball shell sleeved on the ball head, the ball head hinge is provided with a rebounding device, the rebounding device is a spring, one end of the spring is fixed to an edge of the ball shell, the spring is sleeved on the brush rod, and the other end of the spring is fixed to the brush rod.

Figure 8:
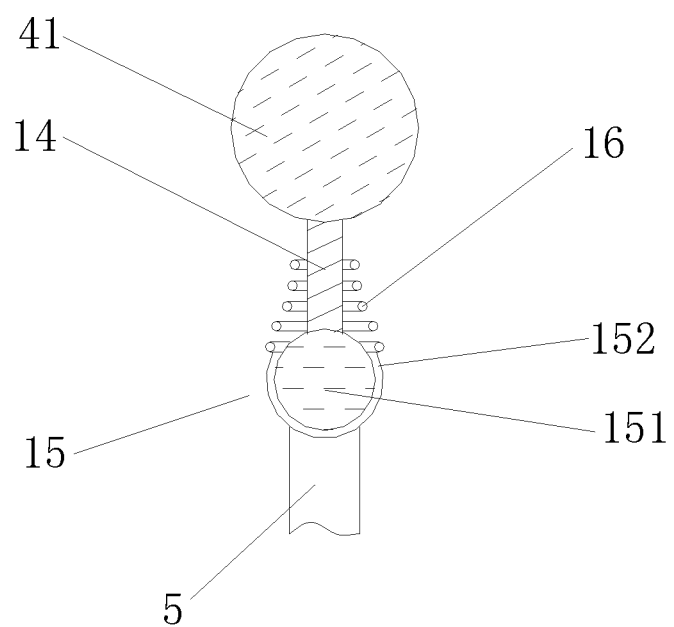
FIG. 8 is an installation schematic diagram of a rebounding device after removing bristles in Embodiment II of the present disclosure.

Referring to FIG. 8 separately, the ball head hinge includes a ball head and a ball shell sleeved on the ball head, the ball head hinge is provided with a rebounding device, which is a spring, the spring is on the short bar or brush bar, and the other end of the spring is fixed to the short bar or brush rod. When the ball head brush is squeezed by the appropriate external force, it will be easily deflected, and make a preparation gesture for bending the brush rod. When the external force disappears, the ball head brush can rebound by the external force, that is, the ball head brush can be straightened, which can not only ensure the smooth bending of the brush rod in order to fit the shape of the uterine cavity, but also reaches a wider sampling range, allows the ball head brush to maintain a suitable tension and always close to the inner wall of the uterus, thereby ensuring the sampling effect of the ball head brush.

The above description is presented only as an enforceable technical solution of the present disclosure, not as a single restriction on the technical solution itself.

What is claimed is:

1. A female reproductive system sample collector, comprising a sampling device and an elution preservation device, wherein an exterior of the sampling device is packaged by a sealing bag, and the elution preservation device is filled with an elution preservation solution; the sampling device being submerged in the elution preservation solution of the elution preservation device and sealed for preservation;

the sampling device comprises a sampling rod and a cylindrical sheath sleeved outside the sampling rod, the sampling rod comprises an operating rod, a straight rod brush and a ball head brush which are connected; the straight rod brush comprises a brush rod and bristles planted on the brush rod, and the ball head brush comprises a ball body connected to a front end of the brush rod and bristles planted on the ball body;

a length of the sheath is greater than or equal to a total length of the straight rod brush and the ball head brush; and an outer diameter of the sheath is less than an inner diameter of the elution preservation device; and a via hole is formed in a lower end cover of the sheath, and the operating rod is threaded in the via hole; a front end of the sheath is provided with an opening and closing cover that prevents loss of a sample, the opening and closing cover corresponds to a position of the ball head brush and comprises four oscillating rods that are hinged with a front port of the sheath and in an uniform and circumferential array around a central axis of the sheath, two oscillating rods are connected through a thin film, the four oscillating rods comprise upper arc-shaped rods and lower L-shaped rods, and hinge points of the oscillating rods are located at corners of the L-shaped rods.

2. The collector according to claim 1, wherein the bristles of the straight rod brush and the bristles of the ball head brush all comprise base bristles at bottom layers and dispersing bristles connected to tail ends of the base bristles, and each base bristle is connected with at least two of the dispersing bristles; independently and optionally, tail ends of the dispersing bristles are connected with secondary dispersing bristles, and each dispersing bristle is connected with at least two of the secondary dispersing bristles.

3. The collector according to claim 1, wherein the sheath includes an inwardly recessed snap ring, the operating rod includes a front neck and a rear neck that are inwardly recessed; the front neck and the rear neck are both circular grooves, and the snap ring is matched with the front neck and the rear neck in size.

4. The collector according to claim 3, wherein a front side wall and a rear side wall of the snap ring are in an inclined shape, and an included angle between the front side wall and the side wall and the side wall of the sheath is 30-70 degrees;
a rear side wall of the front neck is in an inclined shape, an included angle between the rear side wall and the side wall of the operating rod is 30-70 degrees, and a front side wall of the front neck is perpendicular to a side wall of the operating rod; and
a front side wall of the rear neck is in an inclined shape, an included angle between the front side wall and the side wall of the operating rod is 30-70 degrees, and the rear side wall of the rear neck is perpendicular to the side wall of the operating rod.

5. The collector according to claim 4, wherein the elution preservation device is a test tube with a sealing cap, which is in threaded connection or buckling connection with the test tube;

the operating rod is provided with scale marks, and a zero scale position of each scale mark is a foremost end of the ball head brush; and
an outside convex sealing ring is disposed on the outer wall of the sheath, a diameter of the sealing ring surpasses an internal diameter of the elution preservation device by at least 1 mm, and the sealing ring is located at the front of the snap ring.

6. The collector according to claim 1, wherein a diameter of the straight rod brush gradually increases from bottom to top; a diameter of the ball head brush is larger than space enclosed by lower ends of the L-shaped rods, so that the ball head brush is prevented from escaping from the clearance of the L-shaped rods when being retracted, thereby ensuring to closing the opening and closing cover of the collector when the ball head brush touches with the L-shaped rods.

7. The collector according to claim 1, wherein the brush rod is an elastic rod, a maximum deflection of a tail end of the brush rod is 4-5 cm, a ball body of the ball head brush is connected with the tail end of the rod brush through a short rod and a ball head hinge, an oscillating angle of the ball head hinge with the axis of the operating rod as a center is less than or equal to 60 degrees, and bristles are also arranged on the short rod; and a bending rigidity EI of the brush rod is calculated according to the following formula:

$$EI = \frac{5ql^4}{384 Y_{max}},$$

where EI is the bending rigidity of the brush rod, q is the uniform distribution force of the inner wall of the uterine cavity to the brush rod, l is the length of the brush rod, and Ymax is the maximum deflection of the brush rod; and an outer wall of a cross section of the sheath is wavy.

8. The collector according to claim 1, wherein a maximum outward oscillating angle of each oscillating rod in an open status is 40-50 degrees; and when each oscillating rod is completely opened, the thin film is in a tensioned state and the opening and closing cover is in an inverted umbrella shape.

9. The collector according to claim 8, wherein a profile formed by each oscillating rods in a closed state is a hemisphere with a hole in a top center, and the ball head brush is spherical or ellipsoidal.

10. The collector according to claim 1, wherein a length of the sampling rod is 26±2 cm, a length of the straight rod brush is 3.5±0.5 cm, a diameter of a lower end of the straight rod brush is 0.5 cm, a diameter of an upper end of the straight rod brush is 1 cm, a length of the sheath is 8.0±2.0 cm, and a diameter of the ball head brush is 1±0.5 cm.

* * * * *